United States Patent [19]
Bye et al.

[11] Patent Number: 5,593,685
[45] Date of Patent: Jan. 14, 1997

[54] RANITIDINE COMPOSITIONS

[75] Inventors: Alan Bye, Greenford; Jill Evans; Paul D. Huckle, both of Ware; Laurence F. Lacey, Greenford; Peter J. Rue, Ware, all of Great Britain

[73] Assignee: Glaxo Group Limited, London, England

[21] Appl. No.: 411,664

[22] PCT Filed: Oct. 11, 1993

[86] PCT No.: PCT/EP93/02763

§ 371 Date: Apr. 11, 1995

§ 102(e) Date: Apr. 11, 1995

[87] PCT Pub. No.: WO94/08560

PCT Pub. Date: Apr. 28, 1994

[30] Foreign Application Priority Data

Oct. 13, 1992 [GB] United Kingdom .................. 9221414

[51] Int. Cl.⁶ ...................................................... A61K 9/20
[52] U.S. Cl. ........................ 424/439; 424/440; 424/441; 424/465; 424/489; 514/974
[58] Field of Search .................................. 424/465, 441, 424/439, 440, 464, 489; 514/974

[56] References Cited

U.S. PATENT DOCUMENTS

| | | | |
|---|---|---|---|
| 5,075,114 | 12/1991 | Roche | 424/470 |
| 5,084,278 | 1/1992 | Mehta | 424/441 |

FOREIGN PATENT DOCUMENTS

| | | |
|---|---|---|
| 0349103 | 1/1990 | European Pat. Off. . |
| 0459695 | 12/1991 | European Pat. Off. . |
| 0473431 | 3/1992 | European Pat. Off. . |
| 0523847 | 1/1993 | European Pat. Off. . |
| 0538034 | 4/1993 | European Pat. Off. . |
| 2218333 | 11/1989 | United Kingdom . |
| 9217161 | 10/1992 | WIPO . |
| 9221328 | 12/1992 | WIPO . |

*Primary Examiner*—James M. Spear
*Attorney, Agent, or Firm*—Bacon & Thomas

[57] ABSTRACT

The present invention provides a chewable ranitidine tablet comprising ranitidine, or a physiologically acceptable salt thereof, a chewable base selected from sucrose, glucose, lactose, maltose, or a mixture thereof, a flavouring and, optionally, an intense sweetener and a process for its preparation.

18 Claims, No Drawings

RANITIDINE COMPOSITIONS

This application is a 371 of PCT/EP93/02763 filed Oct. 11, 1993.

The present invention relates to improvements in the formulation of the histamine $H_2$-receptor antagonist ranitidine, particularly for oral administration.

Ranitidine, N-[2-[[5-[(dimethylamino)methyl]-2-furanylmethyl]-thio]ethyl]-N'-methyl-2-nitro-1,1-ethenediamine, and its physiologically acceptable salts are described and claimed in British Patent Specification No. 1565966, and a particular crystalline form of ranitidine hydrochloride is described and claimed in British Patent Specification No. 2084580B. In both these specifications there is reference to formulations for oral administration, which may take the form of for example tablets, capsules, granules, powders, solutions, syrups, suspensions, or tablets or lozenges for buccal administration. Oral preparations of ranitidine are also disclosed in British Patent Specification Nos. 2142820, 2198352, 2218336, 2219940, 2222772 and 2229094.

Oral administration constitutes a preferred route for administering ranitidine. Ranitidine, however, in common with many drug substances, has an inherently bitter taste, and this constitutes a disadvantage with certain types of oral preparation. Moreover, it is well known that patients may not complete a necessary course of medicine if they are prescribed an oral presentation which is particularly unpleasant to taste. The problems resulting from the bitter taste of ranitidine are particularly acute in formulations such as chewable tablets.

Chewable tablets are a particularly convenient form of oral presentation for patients who prefer not to take swallowable tablets, or find difficulty in swallowing them.

We have now discovered a chewable tablet formulation which effectively masks the bitter-taste of ranitidine and which also exhibits particularly advantageous bioavailability.

Thus the present invention provides a chewable ranitidine tablet comprising ranitidine, or a physiologically acceptable salt thereof, a chewable base selected from sucrose, glucose, lactose, maltose, or a mixture thereof, a flavouring and, optionally, an intense sweetener.

Chewable ranitidine tablets containing sucrose are described in GB2222772. However, these tablets contain alginic acid and sodium bicarbonate as essential components of the formulation and such tablets are excluded from the present invention.

Thus according to a further aspect the present invention provides a chewable ranitidine tablet consisting essentially of ranitidine, or a physiologically acceptable salt thereof, a chewable base selected from sucrose, glucose, lactose, maltose, or a mixture thereof, a flavouring and, optionally, an intense sweetener.

According to a further aspect the present invention provides a composition consisting essentially of ranitidine, or a physiologically acceptable salt thereof, a chewable base selected from sucrose, glucose, lactose, maltose, or a mixture thereof, a flavouring and, optionally, an intense sweetener.

Ranitidine may be employed in the tablets according to the invention in the form of either its free base or a physiologically acceptable salt. Such salts include salts with inorganic or organic acids such as the hydrochloride, hydrobromide, sulphate, acetate, maleate, succinate, citrate, tartrate, fumarate and ascorbate salts. A particularly preferred salt of ranitidine is the hydrochloride.

The bitter-taste of ranitidine is effectively masked in the chewable tablets according to the invention when ranitidine is employed in conventional form. However, coated or encapsulated forms of ranitidine may be used in the tablets according to the invention. Suitable coated and encapsulated forms are described in, for example, EP538034, EP523847, WO92/21328, EP473431, EP459695, EP349103, CA2068366 and U.S. Pat. No. 5,084,278. Ranitidine resin adsorbates as described in UK2218333 may also be incorporated into the tablets according to the present invention.

Preferably ranitidine and its salts are used in conventional form.

The chewable base in the tablets according to the invention is preferably sucrose. The flavouring in the tablets according to the invention is a strong flavouring such as fruit flavours and natural or synthetic mint or peppermint flavours. Strong mint or peppermint flavourings are preferred.

Intense sweeteners for use in the present invention include for example saccharin or, more preferably, aspartame. Preferably an intense sweetener is present.

Thus according to a further aspect the present invention provides a chewable ranitidine tablet consisting essentially of ranitidine, or a physiologically acceptable salt thereof, sucrose, a flavouring and an intense sweetener.

According to a yet further aspect the present invention provides a chewable ranitidine tablet consisting essentially of ranitidine hydrochloride, sucrose, a flavouring and an intense sweetener.

Preferably the ratio of ranitidine, or its physiologically acceptable salt, to chewable base, flavouring and intense sweetener in the compositions according to the invention are (by weight):

| | | |
|---|---|---|
| ranitidine: (or physiologically acceptable soft) | chewable base | 1:85 to 1:15 |
| ranitidine: (or physiologically acceptable soft) | flavouring | 1:1.5 to 1:0.30 |
| ranitidine: (or physiologically acceptable soft) | intense sweetener | 1:1.35 to 1:0.25. |

Thus preferably the ratio of ranitidine, or a physiologically acceptable salt thereof,: chewable base:flavouring:intense sweetener in the compositions according to the invention ranges from 1:85:1.5:1.35 to 1:15:0.30:0.25 by weight.

The pharmaceutical compositions according to the invention may also contain other excipients conventional to the art such as fillers, binders, disintegrants, lubricants and dessicants. Suitable excipients are well-known to those skilled in the art.

Suitable binders include methylcellulose, sodium carboxymethylcellulose, hydroxypropyl methylcellulose, alginic acid, ethylcellulose, acacia, gelatin, pregelatinised starch, sucrose syrup, polyvinylpyrrolidone (povidone) and guar gum.

A preferred binder is polyvinylpyrrolidone (povidone).

Suitable lubricants include magnesium stearate, zinc stearate, calcium stearate, stearic acid, sodium stearyl fumarate, hydrogenated vegetable oils, glyceryl palmitostearate, glyceryl behenate, sodium benzoate, sodium lauryl sulphate, magnesium lauryl sulphate, mineral oil, talc and mixtures thereof.

Magnesium stearate is a preferred lubricant.

Suitable dessicants include silica gel.

The amount of ranitidine, preferably in the form of a physiologically acceptable salt, particularly ranitidine hydrochloride, in the composition according to the invention is preferably in the range of 10 to 800mg per dosage unit (for example per tablet), e.g. 20 to 600mg, more preferably 25 to 300mg, such as 25, 75, 125 or 150mg, expressed as the weight of free base.

The unit dose (for example contained in one tablet according to the invention) may be administered up to, for example, 6 times a day depending upon the unit dose used, the nature and severity of the conditions being treated, and the age and weight of the patient. Thus, for example, in the treatment of minor conditions where there is an advantage in lowering gastric acidity such as, for example, acid indigestion, over-indulgence of food or drink, acid stomach, sour stomach, waterbrash/regurgitation, heartburn, such as episodic heartburn, nocturnal heartburn, and meal-induced heartburn, gastritis and dyspepsia, lower and more frequent doses of ranitidine may be used, for example doses in the range of 10–150 mg, e.g. 25–75 mg ranitidine expressed as the weight of free base, administered up to 6 times a day as and when required. For more serious conditions such as duodenal and gastric ulceration, reflux oesophagitis and Zollinger-Ellison syndrome, higher and less frequent doses of ranitidine will be employed, for example 75–600 mg, e.g. 150 mg unit doses administered one to four, preferably once or twice, daily.

The chewable tablets according to the invention may be prepared using the conventional stages of mixing, granulation, drying, blending, compression and packing. For example the required quantities of ranitidine or its salt, chewable base and intense sweetener are dispensed and transferred to a mixer granulator. The materials are blended using the mixer and chopper blades on slow speed. The binder is dissolved in a granulating solvent (for example isopropyl alcohol) and the granulating solution is added to the mixture in the granulator with the blades at slow speed. The mixture is granulated, screened and transferred into the bowl of a fluid bed dryer. After drying the granules are passed through a mill fitted with a suitable screen and weighed. The flavouring, dessicant and lubricant are added and the mixture blended. The resulting granules are compressed using a suitable rotary tablet press.

The following table illustrates non-limiting examples of the pharmaceutical compositions according to the invention.

| Ingredient | Example 1 mg/tablet | Example 2 mg/tablet | Example 3 mg/tablet | Example 4 mg/tablet |
| --- | --- | --- | --- | --- |
| Ranitidine HCl | 28.0 | 84.0 | 140.0 | 168.0 |
| Sucrose | 2268.0 | 2212.0 | 2156.0 | 2617.0 |
| Aspartame | 37.5 | 37.5 | 37.5 | 45.0 |
| Povidone | 50.0 | 50.0 | 50.0 | 60.0 |
| Peppermint Flavour | 41.5 | 41.5 | 41.5 | 50.0 |
| Silica Gel | 50.0 | 50.0 | 50.0 | 30.0 |
| Magnesium Stearate | 25.0 | 25.0 | 25.0 | 30.0 |
| Isopropyl Alcohol + | qs | qs | qs | qs |

+ not present in final product

We claim:

1. A chewable ranitidine tablet consisting essentially of ranitidine, or a physiologically acceptable salt thereof, a chewable base selected from sucrose, glucose, lactose, maltose, or a mixture thereof, a flavouring and, optionally, saccharin or aspartame.

2. A composition consisting essentially of ranitidine, or a physiologically acceptable salt thereof, a chewable base selected from sucrose, glucose, lactose, maltose, or a mixture thereof, a flavouring and, optionally, saccharin or aspartame.

3. A tablet according to claim 1 wherein the chewable base is sucrose.

4. A tablet according to claim 1 containing saccharin or aspartame.

5. A tablet according to claim 1 containing a peppermint flavouring.

6. A tablet according to claim 1 wherein the ratio of ranitidine, or a physiologically acceptable salt thereof, to chewable base is in the range of 1:85 to 1:15 by weight.

7. A tablet according to claim 1 containing ranitidine hydrochloride.

8. A tablet according to claim 1 containing 10 to 800 mg ranitidine, expressed as the weight of free base, per tablet.

9. A tablet according to claim 8 containing 25 to 300 mg ranitidine, expressed as the weight of free base, per tablet.

10. A tablet according to claim 5 containing ranitidine hydrochloride.

11. A tablet according to claim 3 containing saccharin or aspartame.

12. A tablet according to claim 3 containing a peppermint flavoring.

13. A tablet according to claim 4 containing a peppermint flavoring.

14. A tablet according to claim 3 wherein the ratio of ranitidine, or a physiologically acceptable salt thereof, to chewable base is in the range of 1:85 to 1:15 by weight.

15. A tablet according to claim 4 wherein the ratio of ranitidine, or a physiologically acceptable salt thereof, to chewable base is in the range of 1:85 to 1:15 by weight.

16. A tablet according to claim 5 wherein the ratio of ranitidine, or a physiologically acceptable salt thereof, to chewable base is in the range of 1:85 to 1:15 by weight.

17. A tablet according to claim 3 containing ranitidine hydrochloride.

18. A tablet according to claim 4 containing ranitidine hydrochloride.

* * * * *